United States Patent [19]

Ottow et al.

[11] Patent Number: 5,359,054

[45] Date of Patent: Oct. 25, 1994

[54] INITIAL COMPOUNDS FOR THE PRODUCTION OF 10β-H-STEROIDS AND A PROCESS FOR THE PRODUCTION OF THESE INITIAL COMPOUNDS

[75] Inventors: Eckhard Ottow; Gunter Neef; Arwed Cleve; Rudolf Weichert, all of Berlin, Fed. Rep. of Germany

[73] Assignee: Schering Aktiengesellschaft, Berlin und Bergkamen, Fed. Rep. of Germany

[21] Appl. No.: 952,736

[22] PCT Filed: Jun. 3, 1991

[86] PCT No.: PCT/EP91/01017

§ 371 Date: Nov. 30, 1992

§ 102(e) Date: Nov. 30, 1992

[87] PCT Pub. No.: WO91/18917

PCT Pub. Date: Dec. 12, 1991

[30] Foreign Application Priority Data

Jun. 1, 1990 [DE] Fed. Rep. of Germany ....... 4018168

[51] Int. Cl.$^5$ .................. C07J 1/00; C07J 17/00; C07J 21/00
[52] U.S. Cl. .................... 540/4; 540/107; 540/108; 540/114; 540/116; 540/120; 540/36; 540/37; 552/505; 552/612; 552/642
[58] Field of Search .............. 552/612, 642, 505; 540/4, 108, 116, 114, 107, 120, 36, 37

[56] References Cited

U.S. PATENT DOCUMENTS

| | | |
|---|---|---|
| 4,102,907 | 7/1978 | Shephard . |
| 4,272,530 | 6/1981 | Teutsch et al. ............. 424/238 |
| 4,519,946 | 5/1985 | Teutsch et al. ............. 260/239.55 |
| 4,780,461 | 10/1988 | Neef et al. .................. 514/179 |
| 4,900,725 | 2/1990 | Nioue et al. . |
| 4,921,845 | 5/1990 | de Jongh et al. ........... 514/172 |
| 5,182,381 | 1/1993 | Philibert et al. ............ 540/4 |
| 5,187,273 | 2/1993 | Brion et al. ................. 540/4 |
| 5,244,886 | 9/1993 | Scholz et al. ............... 514/175 |
| 5,273,971 | 12/1993 | Scholz et al. ............... 514/176 |

Primary Examiner—Johann Richter
Assistant Examiner—Kimberly J. Kestler
Attorney, Agent, or Firm—Millen, White, Zelano, & Branigan

[57] ABSTRACT

The invention includes compounds of the following formula

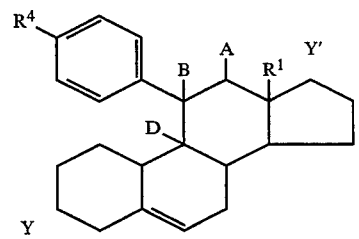

where A and B either A and B form an additional double bond and D is a hydrogen atom or B and D form an additional double bond and A is a hydrogen atom and the other variables are as defined in the specification. Also disclosed is a process of making the compounds and a process of using the compounds to make compounds of the following formula

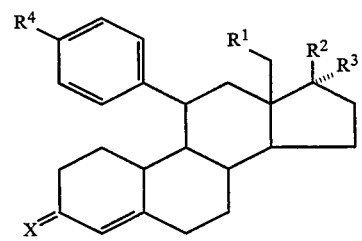

where the variables are defined in the specification. These compounds are useful as antigestigens.

3 Claims, No Drawings

INITIAL COMPOUNDS FOR THE PRODUCTION OF 10β-H-STEROIDS AND A PROCESS FOR THE PRODUCTION OF THESE INITIAL COMPOUNDS

This invention relates to compounds of general formula III

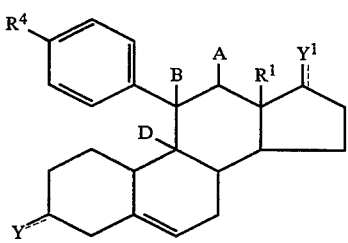

in which
A and B together mean an additional bond and
D means a hydrogen atom or
B and D together mean an additional bond and
A a hydrogen atom
and
$R^4$ stands for a hydrogen atom, a cyano group, a chlorine, fluorine, bromine, iodine atom, for a trialkylsilyl, trialkylstannyl group, for a straight-chain or branched, saturated or unsaturated $C_1$-$C_8$-alkyl, acyl or alkoxyalkyl radical, for an amino group

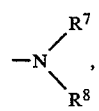

in which $R^7$ and $R^8$ independently of one another mean a hydrogen atom or a $C_1$-$C_4$-alkyl group or for a corresponding amine oxide

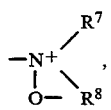

or for the groupings —$OR^9$ or —$S(O)_iR^9$ with i=0, 1 or 2, in which $R^9$ means a hydrogen atom, a methyl, ethyl, propyl, isopropyl, methoxyphenyl, allyl or a 2-dimethylaminoethyl group, or for a heteroaryl radical of formula Iα

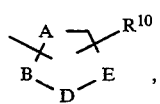

in which A symbolizes a nitrogen, oxygen, or sulfur atom, —B—D—E the element sequence —C—C—C, —N—C—C— or —C—N—C— and $R^{10}$ a hydrogen atom, a cyano group, a chlorine, fluorine, bromine, iodine atom, a trialkylsilyl, trialkylstannyl group, a straight-chain or branched, saturated or unsaturated $C_1$-$C_8$-alkyl, acyl or alkoxyalkyl radical, an amino group

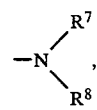

, in which $R^7$ and $R^8$ independently of one another mean a hydrogen atom or a $C_1$-$C_4$-alkyl group, or a corresponding amine oxide

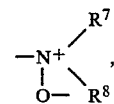

or the grouping —$OR^9$ or —$S(O)_iR^9$ with i=0, 1 or 2 in which $R^9$ means a hydrogen atom, a methyl, ethyl, propyl, isopropyl, methoxyphenyl, allyl or a 2-dimethylaminoethyl group,
or stands for a heteroaryl radical of formula Iβ

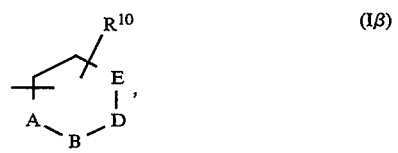

in which A means a nitrogen atom and —B—D—E— the element sequence —C—C—C—, —N—C—C—, —C—N—C— or —C—C—N— and $R^{10}$ has the already indicated meaning,
or stands for a phenyl radical of formula Iγ

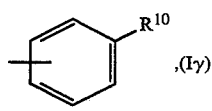

in which $R^{10}$ has the already indicated meaning,
Y and Y' mean a protected keto group or a protected hydroxy group and a hydrogen atom, and Y and Y' can be identical or different, and
$R^1$ means a methyl or ethyl group,
a process for their production and the initial products necessary for this production process.
Preferred are the following compounds:
3,3;17,17-bis-(ethylenedioxy)-11-phenyl-5,11-estradiene,
3,3;17,17-bis-(ethylenedioxy)11-(4-bromophenyl)-5,11-estradiene,
3,3;17,17-bis-(ethylenedioxy)11-(4-methoxyphenyl)-5,9(11)-estradiene,
3,3;17,17-bis-(ethylenedioxy)11-(4-methylphenyl)-5,9(11)-estradiene,
3,3;17,17-bis-(ethylenedioxy)11-phenyl-5,9(11)-estradiene,
3,3;17,17-bis-(ethylenedioxy)11-(4-bromophenyl)-5,9(11)-estradiene,
3,3;17,17-bis-(ethylenedioxy)11-(4-methoxyphenyl)-5,11-estradiene,
3,3;17,17-bis-(ethylenedioxy)11-(4-methylphenyl)-5,11-estradiene.

In addition to the ethylenedioxy group, for example, the 2,2-dimethylpropylene-1,3-dioxy group can also, stand for Y/Y'. Other common protective groups are also possible. If Y and/or Y' stand for a protected hydroxy group and a hydrogen atom, the hydroxy group can be protected, for example as methoxymethyl, methoxyethyl, tetrahydropyranyl or silyl ether.

The compounds of general formula III themselves are used as initial products for the new process for the production of end compounds of general formula I described in the simultaneously filed German patent application . . .

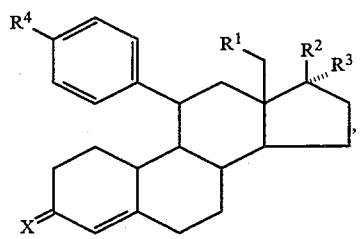

in which

X stands for an oxygen atom, the hydroxyimino grouping >N-OH or two hydrogen atoms, $R^1$ stands for a hydrogen atom or a methyl group, $R^2$ stands for a hydroxy group, a $C_1$-$C_{10}$-alkoxy or $C_1$-$C_{10}$-acyloxy group, $R^3$ stands for a hydrogen atom, the grouping —$(CH_2)_nCH_2Z$, and n is 0, 1, 2, 3, 4 or 5, Z means a hydrogen atom, the cyano group or the radical —$OR^5$ with $R^5$=H, $C_1$-$C_{10}$-alkyl or $C_1$-$C_{10}$-acyl, the grouping —$(CH_2)_m$—C≡C—Y, and m is 0, 1 or 2 and Y means a hydrogen, fluorine, chlorine, bromine or iodine atom, a $C_1$-$C_{10}$-hydroxyalkyl-, $C_1$-$C_{10}$-alkoxyalkyl-, $C_1$-$C_{10}$-acyloxyalkyl radical, the grouping —CH=—CH—$(CH_2)_kCH_2R^6$, and k means 0, 1 or 2 and $R^6$ means a hydrogen, a hydroxy group, a $C_1$-$C_4$-alkoxy- or $C_1$-$C_4$-acyloxy radical, or else $R^2$ and $R^3$ together stand for a radical of formula

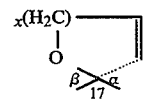

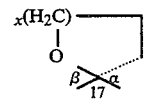

or

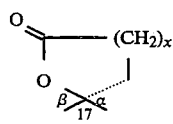

and x = 1 or 2 and $R^4$ has the meaning indicated already in formula III for this substituent.

Also their pharmacologically compatible addition salts with acids belong to the end compounds of general formula I.

The compounds of general formula I themselves have already been described for the most part in German patent application P 39 21 059.6. They are of great interest first of all because of their strong antigestagen properties.

According to this invention the compounds of general formula III are produced in that a compound of general formula IV

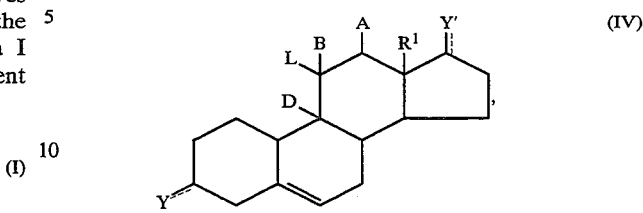

in which A, B and D as well as Y and Y' and $R^1$ that have the meaning indicated in formula III and L stands for a perfluoroalkylsulfonyloxy group $C_nF_{2n+1}SO_2O$—(n=1,2,3,4), in the presence of a catalytic amount of a transition metal catalyst with an aryl compound of general formula V

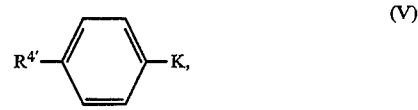

in which K stands for one of the radicals

—B(Alkyl)$_2$
—Sn(Alkyl)$_3$  Alkyl = $C_1$-$C_4$—, alkyl radical
—B(OH)$_2$
—ZnHal
—MgHal    Hal = Cl, Br, J and $R^{4'}$ stands for one of the radicals mentioned under $R^4$, is reacted to a compound of general formula IIIa

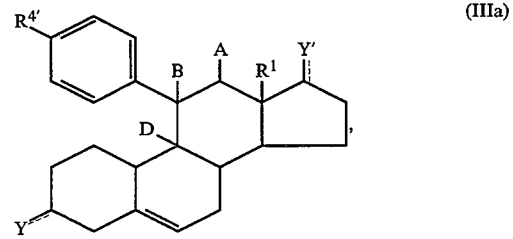

in which A, B and D as well as Y and Y' and $R^1$ have the meaning indicated in formula III and $R^{4'}$ has the meaning indicated in formula V and optionally if $R^4$ in formula III is to have a meaning other than $R^{4'}$ in formula IIIa, a compound of general formula IIIa, in which $R^{4'}$ stands for a bromine atom or after conversion of a methoxy group standing for $R^{4'}$ in a perfluoroalkylsulfonyloxy group $C_nF_{2n+1}SO_2O$— (n=1,2,3,4), is reacted with a compound of general formula VI $R^4$—K    (VI)

in which $R^4$ has the meaning finally desired for this substituent in formula III and K has the meaning already indicated in formula V.

The trifluoromethylsulfonyloxy group preferably stands for L in the compound of general formula IV.

As a transition metal catalyst for coupling the aryl compound of general formula V with the compound having the leaving group L, according to the examples of this invention, acts as a palladiumtetrakistriphenylphosphine (see literature indicated below); nickel tetrakistriphenylphosphine or similar such transition metal catalysts could be used just as well.

The variant that the finally desired substituent $R^4$ is introduced by the functionalization of a bromine or methoxy substituent $R^{4'}$ in compound IIIa, is then to be selected, if the aryl compound of general formula V, in which $R^{4'}$ is already identical with $R^4$, is not available or is not suitable for coupling.

Transition metal catalyzed aryl coupling reactions of compounds of the type of general formula V with compounds that have a leaving group, are described, for example, in: with —Sn(alkyl)$_3$ substituted aromatic compounds: J. E. McMurry and S. Mohanraj, Tetrahydron Letters, 24, No. 27, pp. 2723-2726, 1983; X. Lu and J. Zhu, Communications, pp. 726-727, 1987; Q. -Y. Chen and Z. -Y. Yang, Tetrahedron Letters 27, No. 10, pp. 1171-1174, 1986; S. Cacchi, P. G. Ciattini, E. Morera and G. Ortar, Tetrahedron Letters 27, No. 33, pp. 3931-3934, 1986; A. M. Echavarren and J. K. Stille, J. Am. Chem. Soc. 1987, 109, pp. 5478-5486 and J. Am. Chem. Soc. 1988, 110, p 1557; with —B(OH)$_2$ and -B(0alkyl)$_2$ substituted aromatic compounds: Y. Hoshino, N. Miyaura and A. Suzuki, Bull. Chem. Soc. Jpn. 61, 3008 (1988); H. Matsubara, K. Seto, T. Tahara and S. Takahashi; Bull. Chem. Soc. Jpn. 62, 3896 (1989); with —ZnC$_1$ substituted aromatic compounds: R. McCague, Tet. Lett., 28, 701 (1987); A. Arcadi, A. Burini, S. Cacchi, M. Delmastro, F. Marinelli, B. Pietroni, Syn. Les., 1, 1980, p. 47.

If the substituent $R^{4'}$ in the coupled compound of general formula IIIa is not already the finally desired substituent $R^4$, then compounds of general formula IIIa in the 4-position of the 11-aromatic compound can be further functionalized:

for this purpose either a 4-bromo-phenyl compound IIIa is reacted (EP-A 0349 481, page 11) with a compound of general formula VI $R^4$—K  (VI)

or a 4-methoxy-phenyl compound IIIa is converted by cleavage of the methyl ether, for example with sodium methanethiolate and esterification of the free OH-compound with a perfluoroalkylsulfonic acid anhydride $(C_nF_{2n+1}SO_2)_2O$ (n=1, 2, 3, 4) (P. J. Stang, M. Hanack and L. R. Subramanian, Synthesis 85, (1982)) in the corresponding 4-perfluoroalkylsulfonyloxy-phenyl general formula VI. The coupling of 4-bromine or 4-perfluoroalkylsulfonyloxy-phenyl compound with the compound of general formula VI each takes place by transition metal catalysis according to the methods already cited above. Numerous such coupling reactions especially on steroids that have a trifluoromethanesulfonyloxy group in the 4-position of the 11β-phenyl ring, have already been described in EP-A 0 349 481 and EP-A 0 283 428.

The initial compounds of general formula IV necessary for the process for the production of compounds of general formula III described here are obtainable by reaction of 3,3;17,17-bis-(ethylenedioxy)-5-estren11-one (or an analogous compound with other suitable keto protective groups) with the corresponding perfluoroalkylsulfonic acid anhydride $(C_nF_{2n+1}SO_2)_2O$ [n=1, 2, 3, 4] under basic conditions (M. E. Wright, S. R. Pulley, J. Org. Chem. 1989, 54, 2886).

In addition to the form of the ethylenedioxy ketal, the keto groups can be protected in the way already described above (cf. general formula III).

Preferably the trifluoromethylsulfonyloxy compound is used to obtain the compounds of general formula III.

As the base in the context of this invention, 2,6-ditert.-butyl-pyridine is especially used; however, other pyridine derivatives are also suitable.

The invention is explained below in more detail based on the examples.

EXAMPLES 3,3;17,17-Bis-(ethylenedioxy)-11-trifluoromethylsulfonyloxy-5,9(11)-estradiene 26.1 g (69.7 mmol) of 3,3;17,17-bis-(ethylenedioxy)-5-estren-11-one is dissolved in 350 ml of absolute methylene chloride and mixed under protective gas with 18 ml of 2,6-ditertiary-butylpyridine. After cooling this solution to 0° C., 12.9 ml (76.8 mmol) of trifluoromethanesulfonic acid anhydride is slowly instilled. Then the reaction mixture is stirred for 20 hours more at room temperature. For working up it is poured on saturated sodium bicarbonate solution, the organic phase is separated and the aqueous phase is reextracted with methylene chloride. The combined organic phases are washed with saturated sodium chloride solution, dried on sodium sulfate and concentrated by evaporation in a vacuum. After chromatography of the crude product on silica gel with a mixture of ethyl acetate/hexane 27 g of 3,3;17,17-bis-(ethylenedioxy)11-trifluoromethylsulfonyloxy-5,9(11)-estradiene is obtained as white foam in addition to 16.4 ml of 2,6-di-tertiarybutylpyridine and 5.1 g of 3,3;17,17-bis-(ethylenedioxy)-5-estren-11-one.

$[\alpha]^{20}_D = +104°$ (CHCl$_3$; c=0.505)

$^1$H-NMR(CDCl$_3$) δ: 5.58 ppm (1H,d broad J=5 Hz,H-6); 3.7-4.0 ppm (8H,m,H-ketals); 2.88 ppm (1H,d broad J=11 Hz,H-10); 2.74 ppm (1H,dtr J=16Hz and J=2.5 Hz,H-12); 2.18-2.33 ppm (2H,m,H-4); 0.84 ppm (3H,s,H-18). 3,3,17,17-Bis-(ethylenedioxy)-11-trifluoromethylsulfonyloxy-5,11-estradiene 11.2 ml (80.1 mmol) of diisopropylamine is introduced at −30° C. in 260 ml of tetrahydrofuran under protective gas and mixed with 1.8 ml of a 1.6 molar n-butyllithium solution in hexane. Then the solution is stirred for one hour at 0° C. After instilling of a solution of 10 g of 3,3;17,17-bis-(ethylenedioxy)-5-estren11-one in 130 ml of absolute tetrahydrofuran it is stirred 45 minutes more at 0° C. for deprotonation, then the reaction mixture is cooled down to −78° C. and mixed with 13 ml of trifluoromethanesulfonic acid anhydride by slow instillation. After stirring for2.5 hours more at −78° C. the reaction mixture is poured on saturated sodium bicarbonate solution and the aqueous phase is extracted with ethyl acetate. The combined organic phases are washed with saturated sodium chloride solution, dried on sodium sulfate and concentrated by evaporation in a vacuum. After chromatography of the crude products on silica gel with a mixture of ethyl acetate/hexane, 5.9 g of 3,3;17,17-bis-(ethylenedioxy)11-trifluoromethylsulfonyloxy-5,11-estradiene is obtained as the white foam in addition to 2.4 g of 3,3;17,17-bis-(ethylenedioxy)5-estren-11-one.

Melting point=128°-129° C. (diisopropylether); $[\alpha]^{20}_D = -31°$ (CHCl$_3$; c=0.505)

3,3; 17,17-Bis-(ethylenedioxy)-11-(4-methoxyphenyl)-5,9 (11)-estradiene a) 21.6 g (42.6 mmol) of 3,3; 17,17-bis- (ethylenedioxy) -11-trifluoromethylsulfonyloxy-5,9(11)-estradiene is disson, red in a mixture of 360 ml of toluene and 170 ml of ethanol and mixed in succession with 2.5 g of palladiumtetrakistriphenylphosphine, 3.6 g of lithium chloride, 55 ml of 2 m sodium carbonate solution and 7.2 g (46.8 mmol) of 4-methoxyphenyl boronic acid. The reaction mixture is then stirred for 2 hours at 95° C. cooled to room temperature and mixed with saturated sodium chloride solution. The organic phase is separated, washed in succession with 5% sodium hydroxide solution and water, dried on sodium sulfate and concentrated by evaporation in a vacuum. The residue is chromatographed on silica gel with a mixture of ethyl acetate/hexane. 19.2 g of 3,3;17,17-bis-(ethylenedioxy)11-(4-methoxyphenyl)-5,9(11)-estradiene is obtained as white foam.

b) 1.52 g of 3,3;17,17-bis-(ethylenedioxy)11-trifluoromethylsulfonyloxy-5,9(11)-estradiene is dissolved in 25 ml of absolute dimethylformamide and mixed with 270 mg of lithium chloride and 350 mg of tetrakistriphenylphosphinepalladium. After five minutes more of stirring the reaction mixture is mixed with 1.3 ml of tri-n-butyl-4-methoxyphenyl tin, stirred 3 hours at 110° C. under protective gas, cooled to room temperature and diluted with ethyl acetate. After filtration on celite and washing of the filter residue with ethyl acetate the organic phase is washed with saturated sodium chloride solution, dried on sodium sulfate and concentrated by evaporation in a vacuum. Chromatography of the residue on aluminum oxide (neutral, step III) with a mixture of ethyl acetate/hexane yields 1.15 g of 3,3;17,17-bis-(ethylenedioxy)11-(4-methoxyphenyl)-5,9(11)-estradiene as white foam.

By way of example the preparation of some other products analogously to the above-mentioned specifications a) or b) is listed in the table below:

| aromatic compound (general formula V) | product | yield [%] | physical data |
|---|---|---|---|
| a) 4-Methoxyphenylboronsäure oder<br>b) Tri-n-butyl-4-methoxyphenylzinn | 3,3;17,17-Bis-(ethylendioxy)-11-(4-methoxyphenyl)-5,9(11)-estradien | 97<br>83 | Fp. = 156° C. (Diisopropylether)<br>$[\alpha]_D^{20} = 0,1°$ (CHCl$_3$; c = 0.52) |
| a) 4-Methylphenylboronsäure | 3,3;17,17-Bis-(ethylendioxy)-11-(4-methylphenyl)-5,9(11)-estradien | 92 | Fp. = 175° C. (Diiisopropylether)<br>$[\alpha]_D^{20} = -11°$ (CHCl$_3$; c = 0.505) |
| a) Phenylboronsäure | 3,3;17,17-Bis-(ethylendioxy)-11-phenyl-5,9(11)-estradien | | Fp. = 189° C. (Diisopropylether)<br>$[\alpha]_D^{20} = -3°$ (CHCl$_3$; c = 0.5) |
| a) 4-Bromphenylboronsäure | 3,3;17,17-Bis-(ethylendioxy)-11-(4-bromphenyl)-5,9(11)-estradien | 62 | Fp. = 171° C. (Diisopropylether)<br>$[\alpha]_D^{20} = -15°$ (CHCl$_3$; c = 0.5) |
| a) 4-(Dimethylamino)phenylboronsäure | 3,3;17,17-Bis-(ethylendioxy)-11-[4-(dimethylamino)phenyl]-5,9(11)-estradien | 98 | Fp. = 211° C. (Diisopropylether)<br>$[\alpha]_D^{20} = -48°$ (CHCl$_3$; c = 0.52) | boronsaure = boronic acid
oder = or
zinn = tin
estradien = estradiene
bromphenyl = bromphenyl
ethylendioxy = ethylenedioxy
Fp. = melting point

3,3; 17,17-Bis-(ethylenedioxy)-11-(4-methoxyphenyl)-5,11-estradiene 5.5 g (9.9 mmol) of 3,3;17,17-bis-(ethylenedioxy)11-trifluoromethylsulfonyloxy-5,11-estradiene is dissolved in a mixture of 90 ml of toluene and 40 ml of ethanol and mixed in succession with 0.6 g of palladiumtetrakistriphenylphosphine, 0.85 g of lithium chloride, 13 ml of 2 m sodium carbonate solution and 1.5 g (11 mmol) of 4-methylphenylboronic acid. The reaction mixture is then stirred for one hour at 95° C., cooled to room temperature and mixed with saturated sodium chloride solution. The organic phase is separated, washed in succession with 5% sodium hydroxide solution and water, washed on sodium sulfate and concentrated by evaporation in a vacuum. The residue is chromatographed on silica gel with a mixture of ethyl acetate/hexane. 4.27 g of 3,3;17,17-bis-(ethylenedioxy)11-(4-methoxyphenyl)-5,11-estradiene is obtained as white foam.

By way of example the preparation of some other products analogously to the above-mentioned specification is listed in the table below:

| aromatic compound | product | yield [%] | physical data |
|---|---|---|---|
| 4-Methylphenyl- | 3,3;17,17-Bis-(ethylendioxy)-11- | 88 | Fp. = 152° C. |

-continued

| aromatic compound | product | yield [%] | physical data |
|---|---|---|---|
| boronsäure | (4-methylphenyl)-5,11-estradien | | (Diisopropylether) $[\alpha]_D^{20} = +20°$ (CHCl$_3$; c = 0.505) |
| 4-Methoxy-phenylboronsäure | 3,3;17,17-Bis-(ethylendioxy)-11-(4-methoxyphenyl)-5,11-estradien | 92 | Fp. = 148° C. (Diisopropylether) $[\alpha]_D^{20} = +22°$ (CHCl$_3$; c = 0.505) |
| Phenyl-boronsäure | 3,3;17,17-Bis-(ethylendioxy)-11-phenyl-5,11-estradien | 91 | $^1$H-NMR (CDCl$_3$) δ[ppm]: 7, 12–7, 4(5H, m, H-d J = 1Hz H-12); 5, 6 (1H, d J=5Hz breit, H-6); 1, 0(3H, s, H-18) |
| 4-Bromphenyl-boronsäure | 3,3;17,17-Bis-(ethylendioxy)-11-(4-bromphenyl)-5,11-estradien | 65 | $^1$H-NMR(CDCl$_3$) δ[ppm]: 7, 37(2H, d J=8, 5Hz, H-aromatisch); 7, 05 (2H, d=8, 5Hz, H-aromatisch); 5, 72(1H, d J=1Hz, H-12); 5, 59 1H, d J=5Hz briet, H-6); 0, 96(3H, s, H-18) | boronsaure = boronic acid
aromatisch = aromatic
Bromphenyl = bromophenyl
estradien = estradiene
ethylendioxy = ethylenedioxy
breit = broad
Fp = melting point 3,3;17,17-Bis-(ethylenedioxy)-11-(4-hydroxyphenyl)-5,9(11)-estradiene 9.33 g of 3,3;17,17-bis-(ethylenedioxy)11-(4-methoxyphenyl)-5,9(11)-estradiene is dissolved in 100 ml of absolute dimethylformamide, mixed with 5.6 g of sodium methanethiolate and the reaction mixture is refluxed for 3 hours. After cooling it is poured on water and the aqueous phase is extracted with ethyl acetate. The combined organic phases are washed several times with saturated sodium chloride solution, dried on sodium sulfate and concentrated by evaporation in a vacuum. The residue is chromatographed on silica gel with a mixture of ethyl acetate/hexane and 8.67 g of 3,3;17,17-bis-(ethylenedioxy)-11-(4-hydroxyphenyl)-5,9(11)-estradiene is obtained as white foam.

Melting point=168°-170° C. (ethyl acetate); $[\alpha]^{20}_D = -11°$ (CHCl$_3$; c=0.505)

3,3;17,17-Bis-(ethylenedioxy)-11-(4-trifluoromethylsulfonyloxyphenyl)-5,9(11)-estradiene 4.75 g of 3,3;17,17-bis-(ethylenedioxy)-11-(4-hydroxyphenyl)-5,9(11)-estradiene is dissolved under protective gas together with 8.45 g of 4-dimethylaminopyridine in 160 ml of absolute methylene chloride, cooled to −78° C. and mixed with 2.5 ml of trifluoromethanesulfonic acid anhydride dissolved in 17 ml of absolute methylene chloride. After one hour more of stirring the reaction mixture is poured on saturated sodium bicarbonate solution and the aqueous phase is extracted several times with methylene chloride. The combined organic phases are washed with saturated sodium chloride solution, dried on sodium sulfate and concentrated by evaporation in a vacuum. The residue is chromatographed on silica gel with a mixture of ethyl acetate/hexane and 4.21 g of 3,3;17,17-bis-(ethylenedioxy)-11-(4-trifluoromethylsulfonyloxyphenyl)-5,9(11)-estradiene is obtained.

$^1$H-NMR(CDCl$_3$) δ7.23 ppm (4H,s,H-aromatic); 5.67 ppm (1H,d broad J=5.5 Hz,H-6); 3.74–4.0 ppm (8H,m,H-ketals); 2.94 ppm (1H,d broad J=12.5Hz,H-10); 2.85 ppm (1H,dtr J=16 Hz and J=4Hz,H-12); 0.9 ppm (3H,s,H-18).

3,3;17,17-Bis-(ethylenedioxy)-11-[4-(2-propenyl)-phenyl]-5,9(11)-estradiene a) 3.6 g of 3,3;17,17-bis-(ethylenedioxy)-11-(4-trifluoromethylsulfonyloxyphenyl)-5,9(11)-estradiene is dissolved in 48 ml of absolute dioxane and mixed with 525 mg of lithium chloride and 1.5 g of tetrakistriphenylphosphinepalladium. After stirring for five minutes more the reaction mixture is mixed with 3.8 ml of tributylallyl tin, refluxed for 3 hours under protective gas, cooled to room temperature and diluted with ethyl acetate. After filtration on celite and washing of the filter residue with ethyl acetate, the organic phase is washed with saturated sodium chloride solution, dried on sodium sulfate and concentrated by evaporation in a vacuum. Chromatography of the residue on silica gel with a mixture of ethyl acetate/hexane yields 2.48 g of 3,3;17,17-bis-(ethylenedioxy)11-[4-(2-propenyl) phenyl]-5,9 (11) -estradiene as white foam.

$^1$H-NMR(CDCl$_3$) δ7.03–7.18 ppm (4H,m,H-aromatic); 5.89–6.05 ppm (1H,m,H=CH—); 5.64 ppm (1H,m broad J=5.5Hz,H-6); 4.98–5.1 (2H,m,H-CH$_2$=); 3.7–4.0 ppm (8H,m,H-ketals); 3.37 ppm (2H,d J=6.5 Hz,H-ar-CH$_2$); 3.01 ppm (1H,d broad J=10.5Hz,H-10); 2.84 ppm (1H,dtr J=16 Hz and J=2.5Hz,H-12); 0.92 ppm (3H,s,H-18).

b) 2.05 g of 3,3;17,17-bis-(ethylenedioxy)11-(4-bromophenyl)-5,9(11)-estradiene is dissolved in 80 ml of absolute dioxane and mixed with 200 mg of tetrakistriphenylphosphinepalladium. After stirring for five minutes more the reaction mixture is mixed with 3.9 ml of tributylallyl tin, refluxed for 2 hours under protective gas, cooled to room temperature and diluted with ethyl acetate. After filtration on celite and washing of the filter residue with ethyl acetate the organic phase is washed with saturated sodium chloride solution, dried on sodium sulfate and concentrated by evaporation in a vacuum. Chromatography of the residue on silica gel with a mixture of ethyl acetate/hexane yields 1.71 g of 3,3;17,17-bis-(ethylenedioxy)-11-[4-(2-propenyl)-phenyl]-5,9(11l)estradiene as white foam.

We claim:

1. A compound of formula III

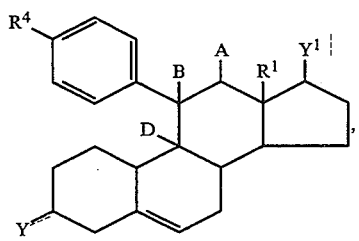
(III)

wherein
A and B together mean an additional bond and D means a hydrogen atom or
B and D together mean an additional bond and A means a hydrogen atom
and
$R^4$ stands for a hydrogen atom, a cyano group, a chlorine, fluorine, bromine, iodine atom, for a trialkylsilyl, trialkylstannyl group, for a straight-chain or branched, saturated or unsaturated $C_1$-$C_8$-alkyl, acyl or alkoxyalkyl radical, for an amino group

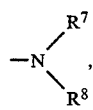

in which $R^7$ and $R^8$ independently of one another mean a hydrogen atom or a $C_1$-$C_4$-alkyl group or for a corresponding amine oxide

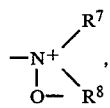

or for the groupings —$OR^9$ or —$S(O)_iR^9$ with i=0, 1 or 2 in which $R^9$ means a hydrogen atom, a methyl, ethyl, propyl, isopropyl, methoxyphenyl, allyl or a 2-dimethylaminoethyl group, or for a heteroaryl radical of formula Iα

(Iα)

in which A symbolizes a nitrogen, oxygen, or sulfur atom, —B—D—E the element sequence —C—C—C, —N—C—C— or —C—N—C— and $R^{10}$ a hydrogen atom, a cyano group, a chlorine, fluorine, bromine, iodine atom, a trialkylsilyl, trialkylstannyl group, a straight-chain or branched, saturated or unsaturated $C_1$-$C_8$-alkyl, acyl or alkoxyalkyl radical, for an amino group

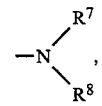

, in which
$R^7$ and $R^8$ independently of one another mean a hydrogen atom or a $C_1$-$C_4$-alkyl group, or stand for a corresponding amine oxide

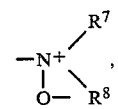

or the groupings —$OR^9$ or —$S(O)_iR^9$ with i=0, 1 or 2, in which $R^9$ means a hydrogen atom, a methyl, ethyl, propyl, isopropyl, methoxyphenyl, allyl or a 2-dimethylaminoethyl group,
or stands for a heteroaryl radical of formula Iβ

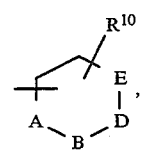
(Iβ)

in which A means a nitrogen atom and —B—D—E—the element sequence —C—C—C—, —N—C—C—, —C—N—C— or —C—C—N— and $R^{10}$ has the already indicated meaning,
or stands for a phenyl radical of formula Iγ

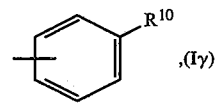
,(Iγ)

in which $R^{10}$ has the already indicated meaning,
Y and Y' means a protected keto group or a protected hydroxy group and a hydrogen atom, and Y and Y' can be identical or different, and
$R^1$ means a methyl or ethyl group.

2. 3,3;17,17-Bis-(ethylenedioxy)11-(4-methoxyphenyl)-5,9(11)-estradiene,
3,3;17,17-bis-(ethylenedioxy)11-(4-methylphenyl)-5,9(11)-estradiene,
3,3;17,17-bis-(ethylenedioxy)11-phenyl-5,9(11)-estradiene,
3,3;17,17-bis-(ethylenedioxy)11-(4-bromophenyl)-5,9(11)-estradiene,
3,3;17,17-bis-(ethylenedioxy)11-(4-methoxyphenyl)-5,11-estradiene,
3,3;17,17-bis-(ethylenedioxy)11-(4-methylphenyl)-5,11-estradiene,
3,3; 17,17-bis-(ethylenedioxy) -11-phenyl-5,11-estradiene,
3,3; 17,17-bis- (ethylenedioxy) -11-(4-bromophenyl)-5,11-estradiene.

3. A compound of formula IV

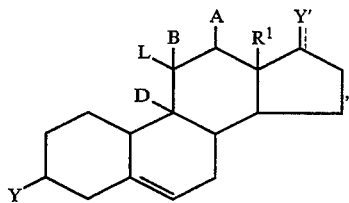

(IV)

wherein

A and B together mean an additional bond and
D means a hydrogen atom or
B and D together mean an additional bond and
A means a hydrogen atom
L means a perfluoroalkylsulfonyloxy group $C_nF_{2n+1}SO_2O-$ (n=1,2,3,4),
$R^1$ means a methyl or ethyl group and
Y and Y' mean a protected keto group or a protected hydroxy group and a hydrogen atom, and Y and Y' can be identical or different.

* * * * *